US009545300B2

(12) United States Patent
Cully et al.

(10) Patent No.: US 9,545,300 B2
(45) Date of Patent: Jan. 17, 2017

(54) FILAMENT-WOUND IMPLANTABLE DEVICES

(75) Inventors: Edward H. Cully, Flagstaff, AZ (US); Joseph A Huppenthal, Flagstaff, AZ (US); Craig T. Nordhausen, Flagstaff, AZ (US); Michael J. Vonesh, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 0 days.

(21) Appl. No.: 11/020,867

(22) Filed: Dec. 22, 2004

(65) Prior Publication Data

US 2006/0136043 A1  Jun. 22, 2006

(51) Int. Cl.
| | |
|---|---|
| *A61F 2/06* | (2013.01) |
| *A61F 2/07* | (2013.01) |
| *A61B 17/00* | (2006.01) |
| *A61B 17/12* | (2006.01) |
| *A61F 2/01* | (2006.01) |
| *A61F 2/90* | (2013.01) |
| *A61F 2/82* | (2013.01) |

(52) U.S. Cl.
CPC ............ *A61F 2/07* (2013.01); *A61B 17/0057* (2013.01); *A61B 17/00234* (2013.01); *A61B 17/12022* (2013.01); *A61B 17/12109* (2013.01); *A61B 17/12113* (2013.01); *A61B 17/12122* (2013.01); *A61B 17/12145* (2013.01); *A61B 17/12172* (2013.01); *A61F 2/01* (2013.01); *A61F 2/82* (2013.01); *A61F 2/90* (2013.01); *A61B 2017/00292* (2013.01); *A61B 2017/00526* (2013.01); *A61B 2017/00575* (2013.01); *A61B 2017/00592* (2013.01); *A61B 2017/00597* (2013.01); *A61B 2017/00606* (2013.01); *A61B 2017/00867* (2013.01); *A61F 2002/011* (2013.01); *A61F 2002/016* (2013.01); *A61F 2002/018* (2013.01); *A61F 2002/072* (2013.01); *A61F 2230/005* (2013.01); *A61F 2230/0006* (2013.01); *A61F 2230/008* (2013.01); *A61F 2230/0065* (2013.01)

(58) Field of Classification Search
CPC .................... A61B 17/0075; A61B 17/12022; A61B 17/12109; A61B 2017/00526; A61F 2/86; A61F 2/90
USPC ...................... 623/1.22, 1.33, 1.15
See application file for complete search history.

(56) References Cited

U.S. PATENT DOCUMENTS

| | | | | |
|---|---|---|---|---|
| 4,629,458 A | * | 12/1986 | Pinchuk | 623/1.47 |
| 4,655,771 A | | 4/1987 | Wallsten | 623/1 |
| 5,015,253 A | * | 5/1991 | MacGregor | 623/1.15 |
| 5,084,065 A | * | 1/1992 | Weldon et al. | 623/1.44 |
| 5,171,262 A | * | 12/1992 | MacGregor | 623/1.15 |
| 5,443,499 A | | 8/1995 | Schmitt | 623/1 |
| 5,556,426 A | * | 9/1996 | Popadiuk et al. | 623/1.33 |
| 5,613,981 A | | 3/1997 | Boyle et al. | |
| 5,628,786 A | * | 5/1997 | Banas et al. | 623/1.13 |
| 5,645,559 A | | 7/1997 | Hachtman et al. | 608/198 |
| 5,674,277 A | | 10/1997 | Freitag | |
| 5,725,552 A | | 3/1998 | Kotula et al. | 606/213 |
| 5,733,294 A | | 3/1998 | Forber et al. | |
| 5,735,892 A | | 4/1998 | Myers et al. | 623/1 |

(Continued)

FOREIGN PATENT DOCUMENTS

| | | |
|---|---|---|
| EP | 699424 | 3/1996 |
| EP | 1158167 | 11/2001 |

(Continued)

*Primary Examiner* — Julie A Szpira

(57) ABSTRACT

A self-expanding implantable medical device formed from one or more non-interlocking filaments. Stents, stent-grafts, occluder devices, and filters are manufactured from one or more filaments utilizing a non-interlocking crossing pattern.

35 Claims, 11 Drawing Sheets

(56) References Cited

U.S. PATENT DOCUMENTS

| | | | |
|---|---|---|---|
| 5,911,731 A * | 6/1999 | Pham et al. | 606/191 |
| 5,968,091 A * | 10/1999 | Pinchuk et al. | 623/1.16 |
| 6,007,574 A | 12/1999 | Pulnev et al. | 623/1 |
| 6,027,529 A * | 2/2000 | Roychowdhury et al. | 623/1.53 |
| 6,123,715 A | 9/2000 | Amplatz | 606/200 |
| 6,217,609 B1 * | 4/2001 | Haverkost | 623/1.22 |
| 6,241,757 B1 * | 6/2001 | An et al. | 623/1.1 |
| 6,488,706 B1 | 12/2002 | Solymar | |
| 6,571,576 B1 | 6/2003 | Lifson et al. | |
| 6,638,257 B2 | 10/2003 | Amplatz | 604/200 |
| 7,235,096 B1 * | 6/2007 | Van Tassel et al. | 623/1.15 |
| 7,445,631 B2 * | 11/2008 | Salahieh et al. | 623/2.18 |
| 8,210,084 B2 * | 7/2012 | An | 87/13 |
| 2004/0093076 A1 * | 5/2004 | White et al. | 623/1.16 |
| 2004/0167611 A1 | 8/2004 | Pulnev et al. | 623/1.15 |
| 2004/0184932 A1 | 9/2004 | Lifson | |
| 2005/0131525 A1 * | 6/2005 | Hartley | 623/1.15 |
| 2005/0149170 A1 * | 7/2005 | Tassel et al. | 623/1.15 |
| 2005/0283962 A1 * | 12/2005 | Boudjemline | 29/433 |
| 2006/0100688 A1 * | 5/2006 | Jordan et al. | 623/1.12 |
| 2014/0172074 A1 * | 6/2014 | Concagh et al. | 623/1.19 |

FOREIGN PATENT DOCUMENTS

| | | | | |
|---|---|---|---|---|
| GB | 1205743 | * | 9/1970 | A61M 29/00 |
| WO | 00/00105 | | 1/2000 | |
| WO | 01/34064 | | 5/2001 | |
| WO | 2004/047681 | | 6/2004 | |

* cited by examiner

FILAMENT-WOUND IMPLANTABLE DEVICES

FIELD OF THE INVENTION

The present invention relates to the field of implantable medical devices, including but not limited to, stents, stent-grafts, occluder devices, and filter devices.

BACKGROUND OF THE INVENTION

Stents, covered stents (i.e., stent-grafts), occluders and filters are commonly used in the treatment of vascular disease, for the creation of shunts between various organs and vessels of the body, for exclusion or sealing of branch vessels or structural defects, and for the reduction of adverse events associated with interventional procedures.

Stents are commonly manufactured from filaments. Nitinol wire is a preferred material given its shape memory properties and excellent history as a material used in implantable devices. Expanded polytetrafluoroethylene (ePTFE) and Dacron® materials are commonly used to cover the stents to create stent-grafts. Covering materials serve to prevent blood passage through the wall of the device and to inhibit the invasion of host tissue or fluids into the lumen of the device. They also are used to isolate aneurysmal vessel pockets from the bloodstream thereby preventing vessel rupture and embolization of plaque or thrombus.

Self-expanding stents and covered stents constructed of filaments are formed by either weaving or braiding multiple filaments. Device removal is imperative in the event of unintentional occlusion of a vessel side-branch, improper device deployment, or if the device is inappropriately sized with respect to the treated vessel segment. Alternatively, devices can be snared and pulled into a catheter or through the vasculature to an access site thereby resulting in the potential for significant damage to the vessel lumen. In instances where significant tissue ingrowth has occurred, removal of such devices is accomplished by the painstaking and time consuming process of removing one filament at a time by pulling on one of its ends. Surgical removal is sometimes necessitated, an outcome that the use of a stent or covered stent is intended to obviate in the first place.

For safety and device durability reasons, both ends of each filament must be secured in some fashion. The design and manufacturing process must guard against the filaments becoming unwoven in use, for instance. This risk must be addressed in the design and construction of the device. As the number of individual filaments in the device increases, the risk of wire pattern disruption at the filament terminations correspondingly increases.

Wallsten, in U.S. Pat. No. 4,655,771, teaches a prosthesis for intraluminal implantation comprising a diametrically expandable or compressible tubular body. This device is preferably a braided tube comprised of flexible and elastic thread elements. When radially compressed and constrained from returning to its original diameter, the inherent self-expansion of this device imparts a hoop force on the wall of the lumen. The patent teaches the formation of crossover points in interlocking relationships, typical of braided structures. The crossover points may optionally be bonded together. Wallsten does not teach the removal of such devices by pulling on the end of a single filament. No teaching is provided for using such a stent to create an occluder device.

Schmitt, in U.S. Pat. No. 5,443,499, teaches a radially expandable tubular prosthesis constructed with yarns that are deformable under dilatation pressures generated by balloon catheter devices. The expansion is achieved by drawing of the yarn within its elastic deformation region or plastically deforming it beyond its yield point. No teaching is presented regarding the use of a resilient filament material that would impart self-expanding properties to the endoprosthesis were it to be radially compressed. The tubular prostheses described therein do not serve the function of a stent or covered stent since they require the addition of a stent fixation device for intraluminal delivery and placement. Also, endoprosthesis plus the stent are not removable by pulling on the end of a single filament and the patent provides no teaching whatsoever regarding the creation of occluder devices.

Myers et al., in U.S. Pat. No. 5,735,892, teach an intraluminal stent graft. The stent graft is comprised of a stent element to which an ePTFE covering is affixed to the exterior surface, the interior surface, or both surfaces of the stent. The stent may be self-expanding or balloon-expandable. The covering can be affixed by an adhesive, preferably fluorinated ethylene propylene (FEP). One embodiment takes the form of a braided structure that employs alternating strand crossover points.

U.S. Pat. No. 6,007,574 and US Published Application 2004/0167611 to Pulnev et al. teach interwoven, interlaced stent devices. They also teach the construction of occlusion devices from these stents. Pulnev et al. do not teach bonding of crossover points.

Kotula et al., in U.S. Pat. No. 5,725,552, and Amplatz, U.S. Pat. No. 6,638,257, teach occlusion devices formed by braiding strands of metal, such as nickel-titanium alloys. The ends of the strands are gathered and held together. These devices are devoid of central orifices through which guidewires could be inserted. The latter patent further teaches the use of a PTFE fabric band around the device periphery in order to inhibit tissue ingrowth. U.S. Pat. No. 6,123,715 to Amplatz teaches the manufacture of similar braided and gathered occlusion devices made of wires such as nitinol.

SUMMARY OF THE INVENTION

The present invention provides implantable medical devices such as stents, stent-grafts, occluder devices, and filters. These devices are manufactured from one or more filaments utilizing a non-interlocking, crossing pattern. As will be further described, the non-interlocking crossing pattern of the devices of the present invention differs from conventional interlocking crossing patterns. With interlocking crossing patterns, a filament or filament portion that is on top of another filament or filament portion at a crossover point is underneath another filament or filament portion at an adjacent crossover point, e.g., braids.

Devices of the present invention are preferably constructed with a single filament. Metallic or non-metallic filaments may be used; however, the filament is preferably a shape memory metal wire, and more preferably a nitinol wire. Small diameter wires are preferred in order to provide the lowest possible device delivery profile. In the case of a single filament construction, the filament is wound around pins of a pin jig in such a manner that for the first winding about the circumference of the pin jig, the filament is wound on top of the surface of the jig. For all subsequent windings, the filament is wound only on top of previously-wound filament, thereby resulting in a non-interlocking winding pattern. Multiple filaments may be wound in a similar fashion. Alternatively, multiple filaments can be wound in succession while still maintaining a non-interlocking pattern.

By "non-interlocking" is meant this winding pattern in which the filament (e.g., a wire) is only wound on top of previously-wound filament; the filament is not passed underneath previously wound filament, nor is the filament woven or braided. A "filament portion" refers to a portion of the length of a filament used to make a device that extends between two apices at opposite ends of the device where the filament is bent to form each of said apices. A pattern is said to be "non-interlocking" if the same wound filament portion is the top filament at three sequentially adjacent crossover points along the length of that filament portion.

The filament is bonded to itself at crossover points thereby creating a stent. The bonds must allow the filament to pivot at the crossover sites in order to enable subsequent processing and compaction of final devices for delivery. Bonding agents can be applied at each filament crossover point. Alternatively, the wire can be provided with a coating of a thermoplastic polymer, allowing the crossover points to be bonded by heating the filament wound device.

More preferably, a wire can be prepared prior to filament winding by helically wrapping it with a length of tape that was cut from a film preferably incorporating an adhesive backing. Acceptable adhesive materials must withstand subsequent processing temperatures. The adhesive is preferably heat-activated. The preferred film is an ePTFE film, more preferably provided with an FEP backing. Preferably, the ePTFE film is both thin and strong. In this embodiment, after the completion of filament winding, the wire-wound pin jig is placed in an oven to melt the adhesive thereby bonding the wire to itself at the crossover points. The device resulting from this process may be used as a stent.

The next step in the creation of an occluder device is to form the stent into a covered stent (i.e., a stent-graft). The term "covered stent" as used herein refers to a stent with a cover attached to its outer surface, a lining attached to its inner surface, or a combination of both. A variety of cover materials can be applied to the stent. In the instance of an occluder, these materials serve as a barrier to fluid flow and as such should be sufficiently fluid impermeable to prevent unacceptable body fluid leakage through the covering for the given occluder application. They must be sufficiently strong to withstand anticipated fluid pressure differentials and cyclical motion. Flexibility is another key attribute of these materials, for they must easily bend during fabrication and in use. Thinness is another desired attribute in order to present a minimal profile at the implantation site within the body conduit. The chosen covering materials must also be biocompatible, and facilitate any desired tissue response, such as tissue ingrowth, tissue incorporation, etc. These covering materials include, but are not limited to, ePTFE, FEP, fluoroelastomers, polyester, silicone, polyurethane, bioabsorbable materials (e.g., polyglycolic acid (PGA), polylactic acid (PLA), trimethylene carbonate (TMC), and copolymers of these) or any combination thereof. The covering material is preferably thin and strong, thereby maintaining a low device profile in order to facilitate delivery to the treatment site. Chosen materials may be porous or non-porous. A preferred stent covering material is ePTFE film having an FEP backing that enables bonding of the covering to the stent during a subsequent heat treatment step.

The resulting covered stent can be subsequently shaped into an occluder or filter device.

Implantable devices according to the present invention may also be created without the covering material (e.g., the above-described stents).

The procedure for forming occluder devices involves placing the covered stent over two colinearly arranged shaping collars separated by a gap. The collars can be placed over a single mandrel or they may be held in place by other suitable means. The portion of the covered stent between the two collars is cinched down and secured by the use of a wire, ePTFE thread, iris, or other means. The two collars are then pushed together, pinching the device between them, thereby holding it in place for the duration of subsequent processing. The ultimate shape of the occluder device is determined by the shape of the collars, whether or not one end of the covered stent is secured to one collar, and where along the longitudinal axis the covered stent is cinched. The diameter and length of the covered stents determined the size of the device. The covered stent so disposed and the shaping fixtures to which it is secured are next placed in an oven in order to heat bond the cover to the wire and to heat set the device into the desired shape. Additional film layers can be bonded to the surface of occluder form if complete sealing of the central mandrel orifice is required for the clinical application.

A tubular device or tubular structure, as described herein, is considered to be a device or structure that is formed about a longitudinal axis. The tubular device or structure is not required to have a constant diameter along its length, and may or may not have an orifice that extends between the ends of the device or structure.

BRIEF DESCRIPTION OF THE DRAWINGS

FIG. 3b is a perspective view of a covered stent on the shaping tool shown by FIG. 3a.

DETAILED DESCRIPTION OF THE DRAWINGS

The present invention relates to the manufacture of implantable devices in the form of stent devices, covered stent devices (stent-grafts), occluder devices and filter devices such as vena cava filters and embolic filters. Heretofore, filament-based implantable device designs have incorporated a filament pattern having interlocking filaments at adjacent crossover points, as would result from weaving or braiding methods of manufacture. Implantable devices 10 of the present invention without interlocking adjacent crossover points (i.e., possessing non-interlocking crossover points) are constructed on a pin jig 14 such as depicted in the perspective view of FIG. 1a. Pin jig 14 is made from a cylindrical mandrel 13 provided with two circumferentially-oriented sets of pins 12 attached to and protruding radially from the surface of mandrel 13. Pins 12 may be attached to mandrel 13 by any suitable method, such as by being inserted into interference-fit holes provided in the surface of mandrel 13.

The two circumferentially-oriented sets of pins 12 include equal numbers of pins. Pins 12 are spaced equal distances apart; the pins 12 at one end of mandrel 13 are preferably aligned with pins 12 at the opposite end of mandrel 13, so that a line drawn through two opposing pins 12 at opposite ends of mandrel 13 is parallel with the longitudinal center line (or axis) of mandrel 13.

Figure 1A:
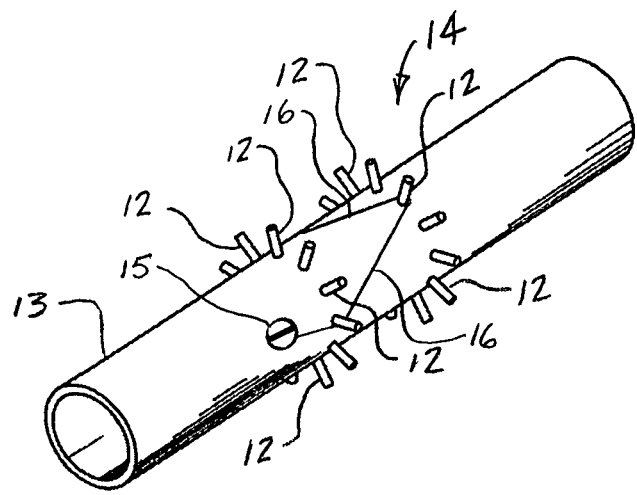
FIG. 1a is a perspective view of a pin jig showing the beginning of the filament winding process.
Figure 1B:
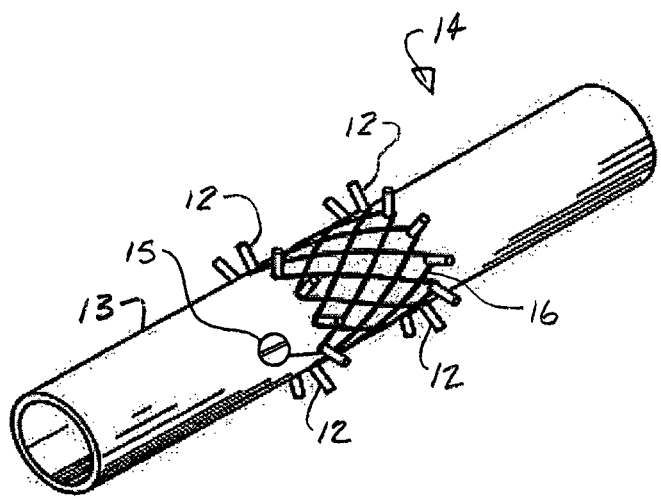
FIG. 1b is a perspective view of a pin jig with a filament wound stent device.

As shown in sequential FIGS. 1a and 1b, the first end of filament 16 is secured to the mandrel by suitable means such as set screw 15. The at least one filament 16 is then wrapped around the pins 12 of pin jig 14, moving alternately between pins 12 at opposite ends of the mandrel and moving circumferentially an equal number of pins (e.g., for the example shown in FIGS. 1a and 1b, moving circumferentially two pins 12 for each winding segment between opposite mandrel ends). With the first full 360 filament winding pass around the circumference of the mandrel, the entire length of the filament 16 is in contact with the surface of the mandrel. For each subsequent 360 degree pass about the circumference of pin jig 14, filament 16 is laid over the previously laid down 360 degree pass of filament 16. The free end of filament 16 is never placed underneath any previously laid down portion of the filament. Winding is complete when the wound filament reaches the first pin 12 at which the winding began. An additional length of filament is provided beyond this first pin in order to provide a suitable length with which to terminate the filament end by bonding to an adjacent length portion as will be further described.

The devices can be made with one or more filaments. The filament is preferably a wire, and more preferably a nitinol wire. While a filament may be a single element or strand, multiple strands (analogous to a multiply stranded cable) may also be used. In making a stent device, the filament is bonded at crossover points of the filament by one of a number of means including gluing with an adhesive, thermal bonding, or attaching by any suitable means.

The use of a single filament 16 is depicted in FIGS. 1a and 1b wherein, prior to beginning the filament winding process, one end of filament 16 is first secured to the outer surface of one end of mandrel 13 by means such as with a screw 15 threaded into the surface of pin jig 14 in a region of the pin jig that does not lie between the two circumferentially-oriented sets of pins 12. The use of securing screw 15 to begin the filament winding process is a preferred method but other methods may also be used. When a single filament is used, the number of pins around the circumference (at any single axial location along the length of the jig) should be an odd number.

Figure 2A:
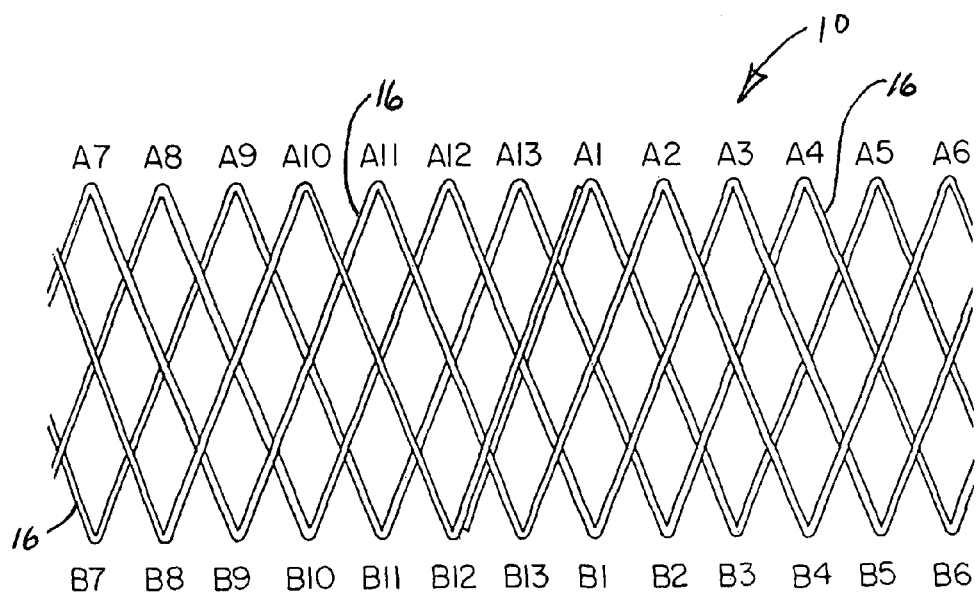
FIG. 2A is the filament pattern used to create a stent of the present invention.

FIG. 2a depicts the outer surface of a device 10 that has been cut longitudinally (i.e., parallel to the longitudinal axis of the tubular device) and laid flat. The illustrated device 10 has been made on a jig having 13 pins in each circle of pins protruding from the surface of the jig. These two circles of 13 pins result in apices A1-A13 at one end of device 10 and corresponding 13 apices B1-B13 at the opposite end of device 10. This view illustrates how the outer windings of filament 16 that have been placed last overlay the previously laid windings of filament 16. Filament wrapping of device 10 began with the end of the underlying filament portion extending from apex B12 toward and continuing around the pin located to produce apex A1. Wrapping of device 10 continued with filament 16 extending to and winding around apex B3, thus offsetting circumferentially by two pins as the filament extends from the "A" end of device 10 to the "B" end. While an offset of two pins between ends of the device is illustrated, other different amounts of offset may be used. Device wrapping was ultimately concluded with the overlying filament portion extending from apex B12 toward and ending at apex A1. The beginning and ending filament portions extending between apices B12 and A1 are parallel to and in contact with each other, except where the contact is interrupted by crossover points of other filament portions. They are bonded to each other where they are in contact by previously described means.

The varying pattern of crossover relationships resulting from the filament winding process is illustrated by FIG. 2a. For example, it is seen that filament portion extending between apices B8 and A10 overlies all crossed filament portions. Adjacent parallel filament portion extending between apices B7 and A9 (immediately to the left of the filament portion extending between apices B8 and A10) underlies all crossed filament portions. Parallel filament portion extending between apices B9 and A11 (immediately to the right of filament portion extending between apices B8 and A10) overlies two crossed filament portions and underlies one filament portion. Continuing to the next parallel filament portion to the right, extending between apices B10 and A12, it is seen that this portion overlies one crossed filament portion and underlies two crossed filament portions. The next adjacent parallel filament portion to the right, extending between apices B11 and A13, underlies all three of the filament portions that it crosses. It is apparent that this variation in crossover relationships between adjacent filament portions results from the filament winding method of making the device of the present invention.

Figure 2B:
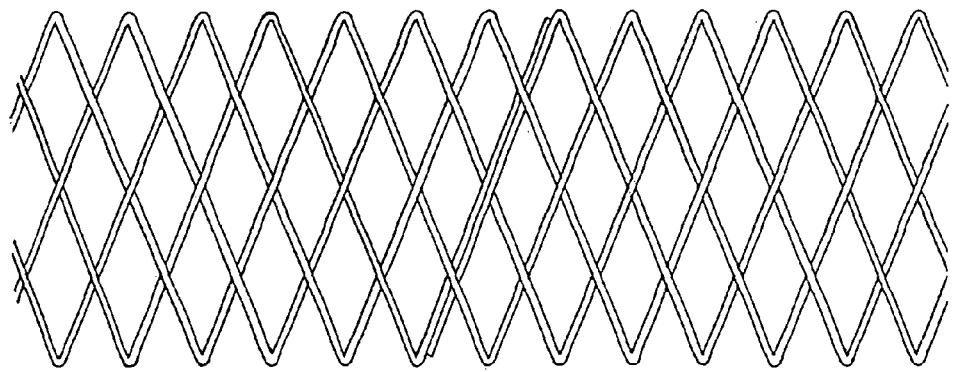
FIG. 2B is a braided filament pattern used in stents of the prior art.

FIG. 2b describes a similar device of the prior art, also cut open longitudinally, that has been made by a conventional braiding or weaving process that results in alternating crossover relationships. Any filament portion that is on top of another filament portion at any given crossover will underlie the next filament portion at any adjacent crossover. This alternating pattern of crossover relationships results from a process of weaving or braiding that requires passing filaments alternately over and under each other. This is entirely different from the process of the present invention wherein the filament winding is accomplished by always winding over previously laid down windings, resulting in the pattern seen in FIG. 2a.

When multiple filaments are used, the number of pins about the circumference at any axial location can be odd or even. The first winding of each filament must wind around a starting pin not previously used. The ends of the filament(s) are preferably bonded adjacent to another portion of a filament.

When winding and subsequent bonding of crossover points is complete, the resulting stent device 10 is removed from the pin jig by gently prying each apex of the device off the pin that it was formed around. The resulting device is a non-woven and non-braided filament-based stent. If made from an appropriate material (e.g., nitinol wire), the stent is a self-expanding stent.

Manufacturing ease is another significant benefit of this design. The number of free ends that must be safely terminated can be as few as two. The number of free ends is, of course, equal to twice the number of filaments used to construct the device. Securing the free ends within the stent frame can be a very time-intensive process, hence, the fewer the ends, the quicker and easier the process.

In forming a covered stent, it is preferable to prepare the filament for eventual covering of the stent prior to winding the filament about the pin jig. A filament that facilitates bonding of a covering to the stent is preferred. A nitinol wire covered with a specially constructed ePTFE film composite is more preferable. A narrow width ePTFE composite film with FEP or another suitable adhesive bonded to one side is well suited for this use. It affords both bonding of the covering to the stent and bonding the covered wire to other covered wire at the crossover points. The composite film is wrapped but not adhered to the wire with the adhesive side facing outwards. The wrapped wire is formed on the pin jig as described above. The wire on the pin jig is heated in an oven above the melt temperature of the adhesive for sufficient time to bond the wire at the crossover points. Care is taken not to subject the chosen materials (e.g., ePTFE or FEP) to thermal conditions that may compromise their mechanical integrity. The assembly is removed from the oven, quenched in water, and the stent is removed from the jig.

The stent is next snugly fit over a cylindrical mandrel and a cover material is applied. Preferably, an ePTFE tube is first placed over the mandrel in order to later facilitate removal of the device from the mandrel. Next, about two layers of film such as the narrow ePTFE-FEP composite film described above is wrapped on top of the ePTFE tube. The film is preferably applied with the FEP side facing outwards such that the longitudinal direction of the film is aligned with the longitudinal axis of the tube. The stent is then slipped over top of the film-covered tube on the mandrel. About two more layers of the ePTFE-FEP composite film, with the FEP side contacting the stent, are wrapped about the stent. The composite film serves as the stent covering, occluder film or filter media. The microstructure of the composite film is selected based upon the intended application. The entire assembly is placed in an oven and heated sufficiently to bond the film device together. The assembly is removed from the oven and quenched. The resulting covered stent is removed from the mandrel and ePTFE tube and the ends of the covering material are trimmed if necessary. The device, following completion of this construction step, is non-woven and non-braided, self-expanding, filament-based stent-graft.

Forming this covered stent device 10 into an occluder device entails placing the covered stent device 10 (comprising filament 16 and covering 33) over a shaping tool 30 (as shown by the perspective view of FIG. 3a) that consists of two shaping collars 31 that slide along a mandrel 34 and are locked into place on mandrel 34 with locking collars 32. The shaping collars 31 are spaced a distance apart so that a portion of the covered stent device 10 can be cinched between the shaping collars 31 to form a small waist. That is, the covered stent 10 in FIG. 3b is positioned over the shaping collars 31 so that both ends are supported by the collars 31 while the middle is positioned over the exposed segment of mandrel 34 between the two shaping collars 31. A fiber 40 as shown in FIG. 4a is then wrapped around the portion of the covered stent 10 that lies between the two collars 31 and is pulled taught thereby cinching the covered stent 10, creating a waist in the device. More wraps of the fiber 40 are added, then the shaping collars 31 are positioned tightly together by moving them together axially as shown by arrows 42 and held in place by the two smaller diameter locking collars 32. With the shaping collars 31 positioned tightly together, it is unnecessary to tie a knot in the cinching fiber, the waist portion of the device 10 being held restrained by the collars 31. The device 10 is then heat-treated as necessary to cause it to assume the new shape.

Figure 4A:
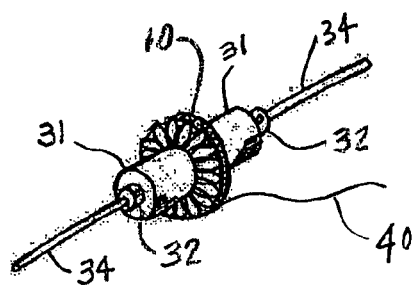
FIG. 4a is a perspective view of a covered stent cinched on a shaping tool for making a flared occluder device.
Figure 4B:
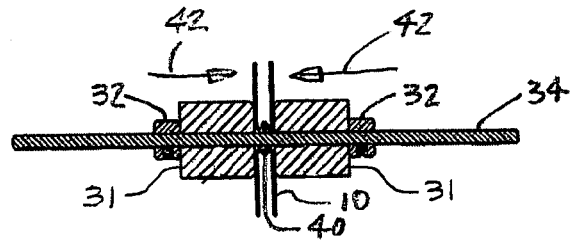
FIG. 4b is a longitudinal cross-section of a covered stent cinched at the middle of its length for making a flared occluder device.
Figure 4C:
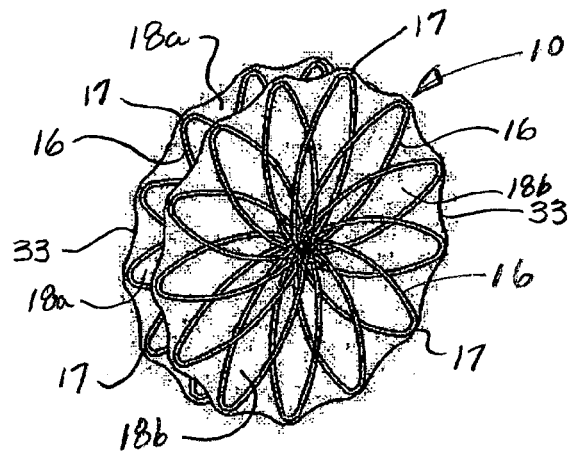
FIG. 4c is a perspective view of a flared occluder device.
Figure 4D:
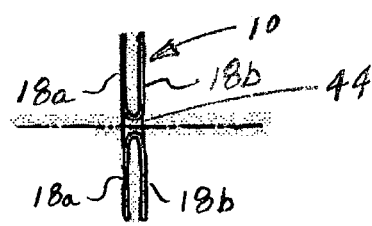
FIG. 4d is a longitudinal cross-section of the flared occluder device of FIG. 4c.

The completed device 10 resulting from this process is shown in the perspective view of FIG. 4c and the longitudinal cross section of FIG. 4d. This occluder device 10 has opposing flattened ends 18a and 18b, each of which comprise portions of the wound filament 16 having, at the perimeter of the device 10, a multiplicity of apices 17. Covering 33 is provided over both opposing flattened ends 18a and 18b.

The presence of the mandrel 34 creates a central orifice 44 in the final occluder device 10 shown in the longitudinal cross section of FIG. 4d. Such an orifice 44 is useful for loading the device 10 onto a guidewire and subsequently delivering the device to the treatment site. Alternatively, orifice 44 may incorporate an additional component such as a valve, filter media, a diagnostic or therapeutic device such as a sensor, etc. Likewise, orifice 44 may be dilatable following implantation using a balloon catheter if desired.

Orifice 44 may be eliminated if desired by covering it with a material (e.g., ePTFE) after the device has been formed. Such a covering over orifice 44 may be desirably punctured by the use of a suitable tool (for retrieval, for example) after implantation.

Alternatively, the diameter of the central orifice 44 can be minimized or eliminated by not using a mandrel that extends between the collars. This is achievable by affixing the shaping collars 31 to the ends of separate mandrels and aligning them on the same longitudinal axis by any suitable means. The center portion of the covered stent 10 can be completely cinched with the use of an iris device (as an alternative to the use of cinching fiber 40), followed by positioning the collars 31 together to hold the cinched region of the device 10 in place.

The size of the device 10 is determined by the size of the precursor covered stent. The shape of the device is largely determined by the shape of the shaping collars 31 and whether or not the covered stent 10 is bound (e.g., tied down with a fiber 40) to a shaping collar 31 during the heat setting process. Device 10 of the present invention as shown in FIGS. 4*a* through 4*d* is a flared occluder device constructed using the shaping tool 30 shown in FIG. 3*a*.

Figure 3A:
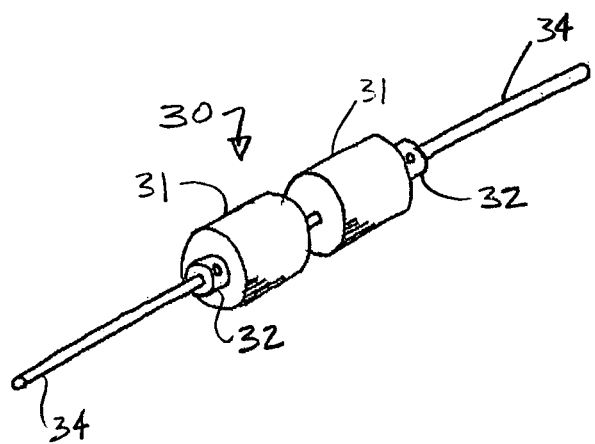
FIG. 3a is a perspective view of a shaping tool for making a flared occluder device.
Figure 3B:
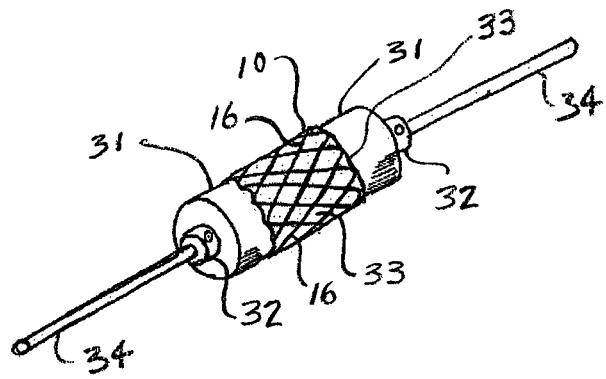
Figure 5A:
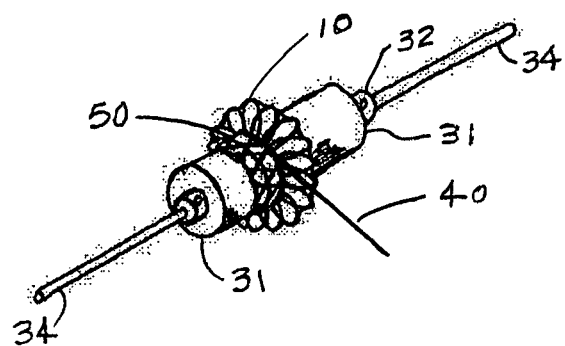
FIG. 5a is a perspective view of a covered stent cinched and secured on a collar of a shaping tool for making a goblet shaped occluder device.
Figure 5B:
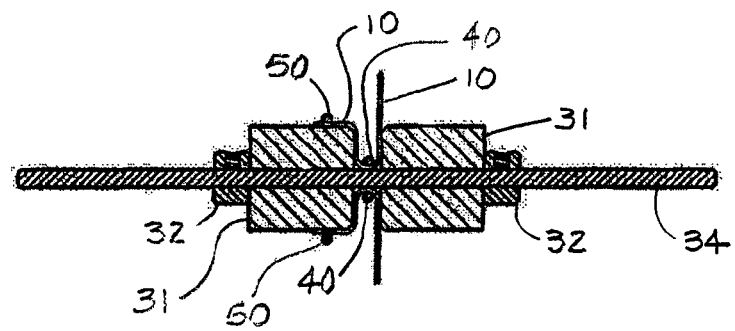
FIG. 5b is a longitudinal cross-section of a covered stent cinched and secured on a collar of a shaping tool for making a goblet shaped occluder device.
Figure 5C:
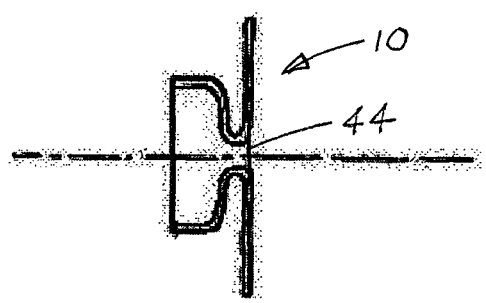
FIG. 5c is a longitudinal cross-section of a goblet-shaped occluder device

Using the same construction of covered stent 10 and the same shaping tool 30 of FIG. 3*a* also enables construction of a goblet-shaped occluder device 10 shown in the longitudinal cross section of FIG. 5*c*. The covered stent 10 is placed over the shaping collars 31 as previously described. In this embodiment, prior to cinching the covered stent 10, a fiber or film 50 is wound around one end of the covered stent 10 in order to secure it to one of the shaping collars 31. The collars 31 are next pushed together, as before, as seen in FIGS. 5*a* and 5*b*. The assembly is placed in an oven to heat set the device into the desired goblet shape. The assembly is removed from the oven, allowed to cool, and the goblet-shaped occluder device 10 is removed from the shaping tool 30.

Figure 6:
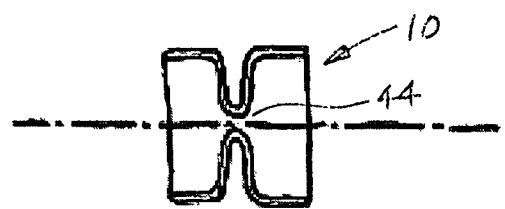
FIG. 6 is a longitudinal cross-section of an hourglass-shaped occluder device.

Hourglass shaped occluder devices 10 as shown by the longitudinal cross section of FIG. 6 can be made in much the same manner that goblet shaped devices of FIG. 5*c* are made. The only significant difference arises when securing the covered stent 10 to the shaping collars 31. Each end of the covered stent 10 is secured to the shaping collar underneath it with a fiber or film or other suitable means. All process steps before and after this step are the same as previously described for making a goblet-shaped device.

Figure 7A:
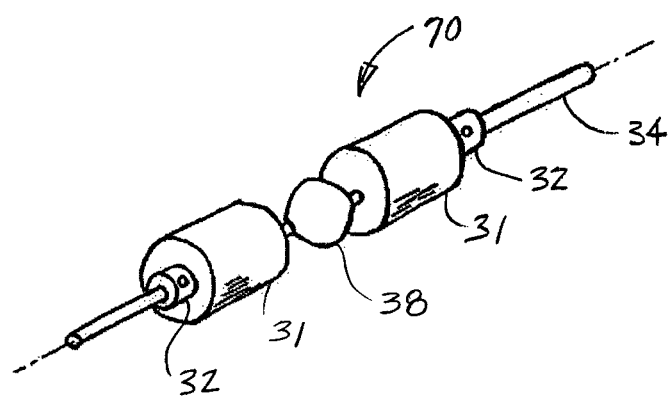
FIG. 7a is a perspective view of a shaping tool for making a pumpkin-shaped occluder device.
Figure 7B:
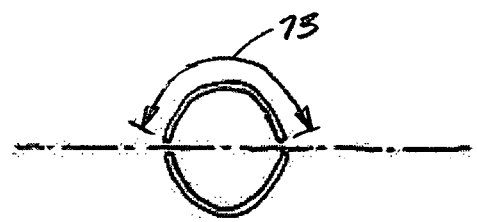
FIG. 7b is a side view of a pumpkin-shaped occluder device.

A spherically-shaped occluder device 10 as shown in the longitudinal cross section of FIG. 7*b* can be made utilizing the shaping tool assembly 70 of FIG. 7*a*. In this case, an additional shaping collar 38 having a spherical shape is fitted over mandrel 34, between the two cylindrical shaping collars 31. The length of the precursor covered stent should correspond to the arc length 73 across the spherical shaping collar 38 (between its opposite ends) as measured parallel to the longitudinal axis so that the ends of the filaments at the formed apices converge to just contact the mandrel between the ends of the spherical shaping collar 38 and the two adjacent shaping collars 31. The ends of the covered stent 10 are forced radially inward toward the mandrel 34 by over-wrapping with any suitable flexible material that will withstand the subsequent heat setting temperature.

It is apparent that the symmetry of any such formed device 10 along the longitudinal axis is further determined by the location of the waist created by cinching with respect to the center point of the precursor covered stent along its longitudinal axis.

Devices of the present invention are preferably constructed using just a single filament. Devices made with only one filament (and not encumbered by additional restraining members) can be cohesively disassembled and removed from the body by pulling on one end of the filament, sequentially disrupting the bonds at the crossover points. Reduced procedural time, decreased risk of trauma to the vessel wall, and improved ease of use are afforded compared to removing devices comprising multiple filaments. Devices of the present invention constructed with multiple filaments can still be removed from the body, but require the removal of one filament at a time.

Figure 8A:
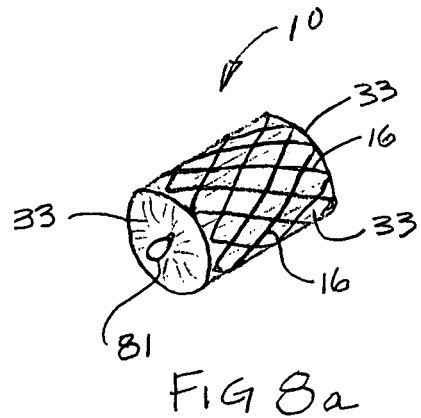
FIG. 8a is a perspective view of an occluder made from a stent-graft wherein the tubular graft covering provided with the stent extends over and encloses one end of the device, rendering it into an occluder device.

The device of the present invention may also be made in forms that are retrievable intact rather than being retrievable by disassembly. FIG. 8A shows a perspective view of an occluder device 10 made as a variation of the above-described covered stent-grafts. In this embodiment, the covering material 33 extends beyond one end of the stent-graft to enclose that end, thereby rendering the stent-graft into an occluder. The covering material 33 is gathered such as by tying in a knot or providing a crimping device (which may be radiopaque) where covering material 33 converges at its intersection with the longitudinal axis of the tubular device. This point of gathering may be optionally provided with a loop 81 or other means whereby the closed end of the device may be grasped by a retrieval tool and drawn into the end of an adjacent catheter for removal from the body in which it had been previously implanted. Retrievability of the device intact is particularly useful immediately after deployment of the device if, for example, it is then decided by the practitioner that the site of deployment is not as desired. The device is then removed, after which it may (for example) be re-deployed at another location or replaced by another device.

Figure 8B:
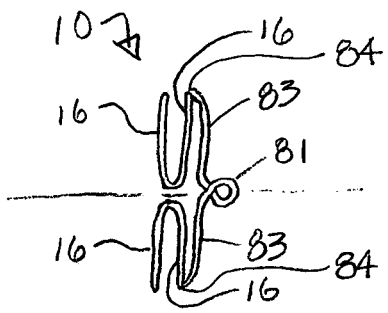
FIGS. 8b-8d are longitudinal cross sections of various embodiments of the occluder device.

In a variation shown by the longitudinal cross section of FIG. 8*b* (based on the device shown in FIG. 4*d*), one end of the device is provided with wire extensions 83 attached to at least two points 84 at the perimeter of the device 10 that converge at loop 81 (or other suitable grasping means) to enable the implanted occluder device 10 to be retrieved into a catheter. The wire extensions 83 may also be integral to the device rather than being separately attached components.

Figure 8C:
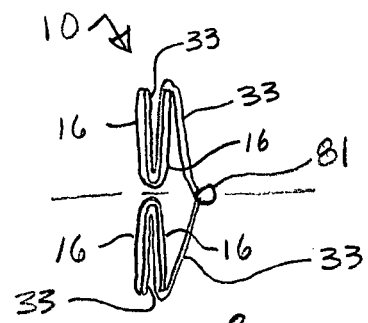

The longitudinal cross section of FIG. 8*c* shows another alternative wherein a covering 33 is provided over the surfaces of occluder 10 (similar to FIG. 4*c*) but extending over one end in the fashion shown by FIG. 8*a*, with the extending covering material converging at a loop 81. The device of FIG. 8*a* may be used as a precursor to make the device of FIG. 8*c*. Additionally, the device 10 may be provided with a purse-string around the outer periphery of the device, for example, threaded through the filament apices. If a covering material is also provided, the purse strings extend back to the center of the covering that extends over the end of the device and are available for grasping by a suitable catheter-delivered retrieval tool. Applying tension to the ends of the purse strings reduces the diameter of the device 10 in order to enable it to be adequately collapsed for being drawn into the lumen of the retrieval catheter.

The purse strings may be attached to device 10 whereby they extend back to the medical practitioner via the delivery catheter for use during the delivery procedure. As such, they may be utilized by the practitioner immediately following implantation if it is immediately decided that the implant is unacceptable for any reason. The purse strings are most preferably provided as a single length of purse string, extending from the proximal end of the catheter (i.e., the end accessible to the practitioner) through a first catheter lumen (in the delivery catheter) to the device 10, continuing around through the filament apices at one end of device 10, and extending back to the practitioner, preferably through a second catheter lumen independent from the first. The application of tension to both ends of the purse string causes the diameter of device 10 to be reduced as necessary to enable it to be pulled back into the catheter if that is desired. Alternatively, if it is concluded that the device 10 is deployed and functioning as intended, the purse string may be removed by pulling on either of the two ends of the purse strings, thereby withdrawing the entire length of the purse string.

Figure 8D:
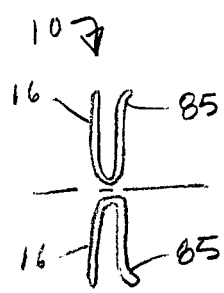

For any of the embodiments described by FIGS. 8b and 8c, the device 10 may optionally be formed with slightly bent filaments 85 adjacent the apices of one end as shown by longitudinal cross section of FIG. 8d. This is anticipated to make it easier to pull the device back into a retrieval catheter. The bent filaments adjacent the apices may be formed by forcing the apices against the adjacent ends of appropriately modified shaping mandrel collars prior to heat treatment. It is apparent that only selected apices may be bent, or if desired, all apices may be bent.

Figure 8E:
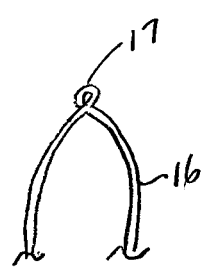
FIGS. 8e and 8f are detail end views of filaments formed to create alternatively shaped apices.
Figure 8F:
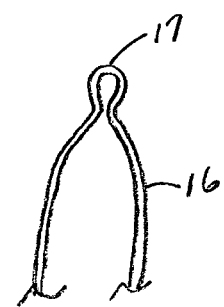

As shown by the exemplary detail end views of FIGS. 8e and 8f, apices 17 may be desirably provided with various alternative bent forms.

Figure 9A:
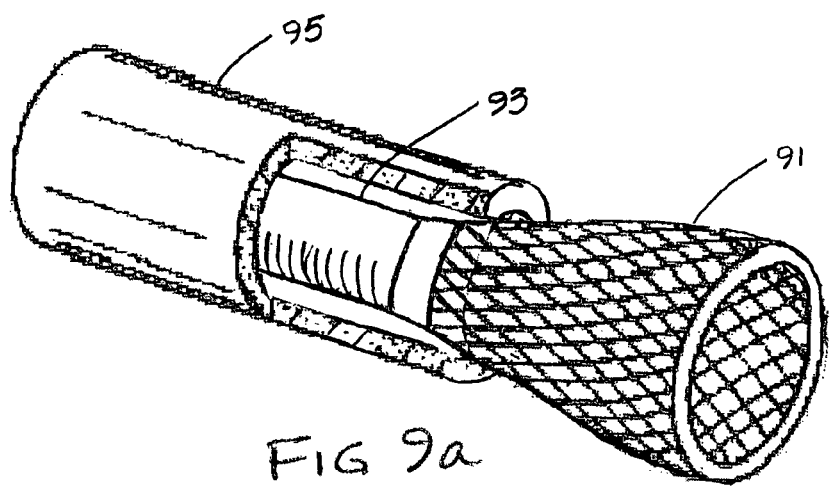
FIG. 9a is a perspective view of a catheter delivery and retrieval system for use with the implantable devices.

It may be useful to use coaxial catheters to effect retrieval of devices of various types (e.g., occluders, vena cava filters) as shown by the perspective view of the catheter delivery and retrieval system illustrated by FIG. 9a. A funnel-shaped wire mesh snare 91 is provided affixed to the distal end of a first catheter 93, which is delivered to the retrieval site by an outer, coaxial catheter 95. Extending the inner catheter 93 beyond the distal end of the outer catheter 95 allows the snare 91 to be deployed, allowing its distal end to self expand to a larger diameter at which it may be used to capture a device 10. Withdrawing inner catheter 93 back into outer catheter 95 forces snare 91 back to a smaller diameter, thereby retaining a captured device within snare 91. This snare 91 may also be included as a portion of the catheter delivery system enabling acute retrieval of a device 10 is that should be desired following a deployment of device 10 that is deemed unsatisfactory for any reason.

Snare 91 may be made of a variety of filamentary materials; nitinol wire is preferred for the self-expanding characteristic desired for best performance of snare 91. The snare 91 may be of woven or braided construction, but may also be made using the filament winding method described previously. The filament used to make the snare may optionally be provided with a coating or covering material over the surface of the filament (e.g., ePTFE tape helically wrapped over the filament surface). Likewise, snare 91 may also be provided with a covering (e.g., ePTFE film) in the fashion of a covering over a stent to achieve a stent-graft.

Figure 9B:
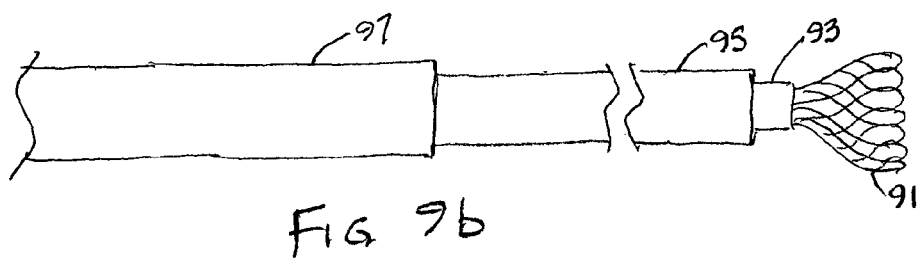
FIGS. 9b and 9c are sequential side views of an alternative catheter delivery and retrieval system incorporating a secondary filter component.
Figure 9C:
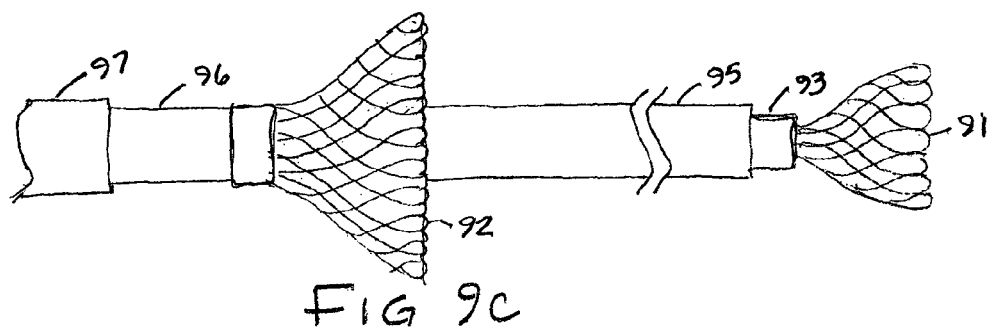

FIGS. 9b and 9c are sequential side views of an alternative catheter delivery and retrieval system incorporating a secondary filter component. FIG. 9b shows the system with an introducer catheter 97. This system further includes an auxiliary filter 92 shown deployed in FIG. 9c by withdrawal of introducer catheter 97 from the filter 92 and its associated catheter 96. The direction of fluid flow in the body conduit (not shown) is toward the open end of auxiliary filter 92. Such an auxiliary filter 92 may be useful for procedures where a concern exists that removal of an implanted device by the use of a tool such as snare 91 may result in undesired release of emboli.

Figure 9D:
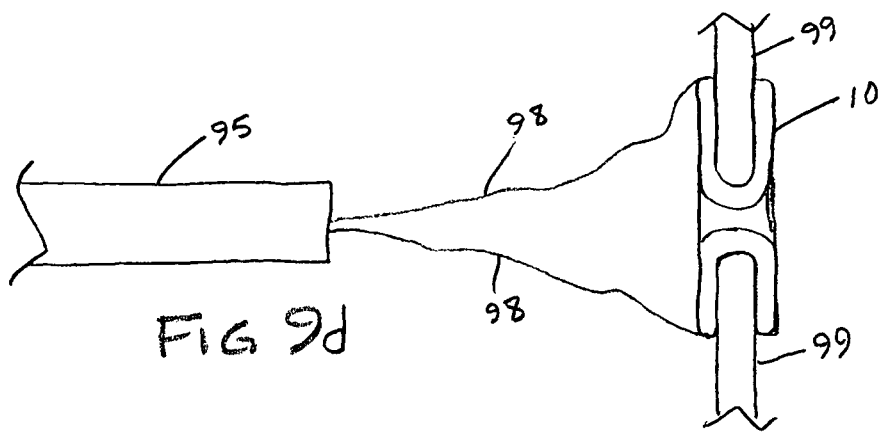
FIGS. 9d-9j are side views of the catheter delivery and retrieval system as it would be used to retrieve an implantable device.
Figure 9E:
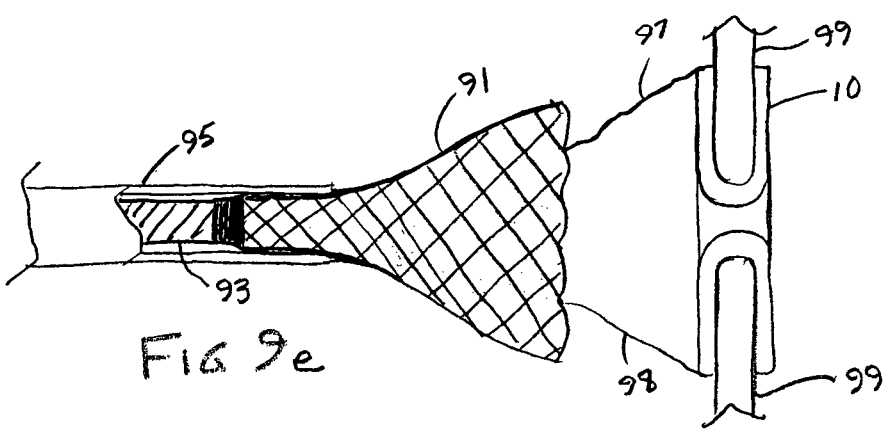
Figure 9F:
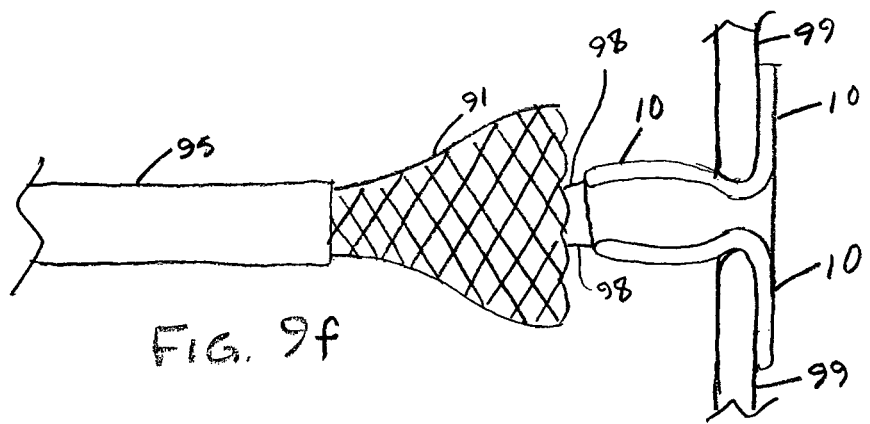
Figure 9G:
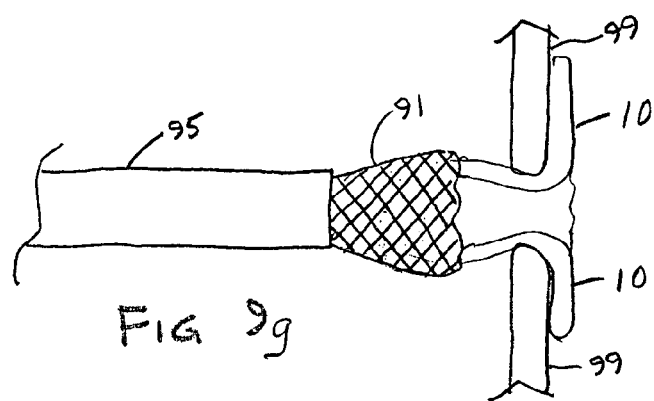
Figure 9H:
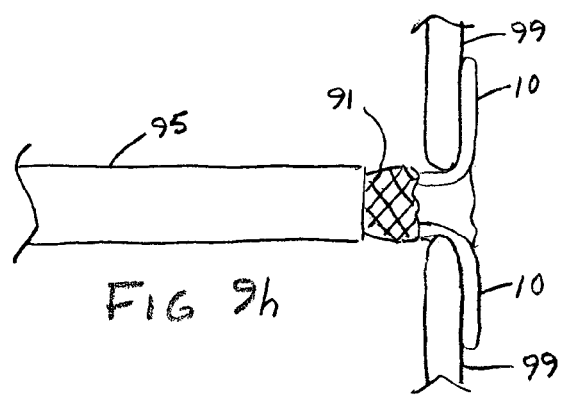
Figure 9I:
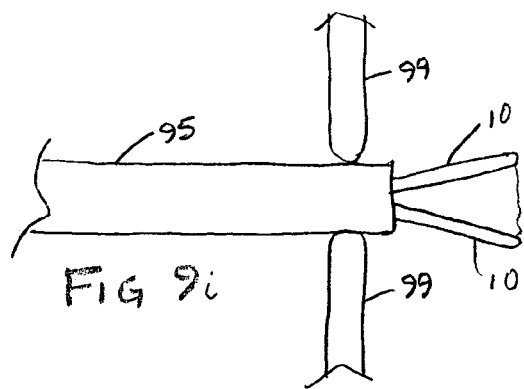
Figure 9J:
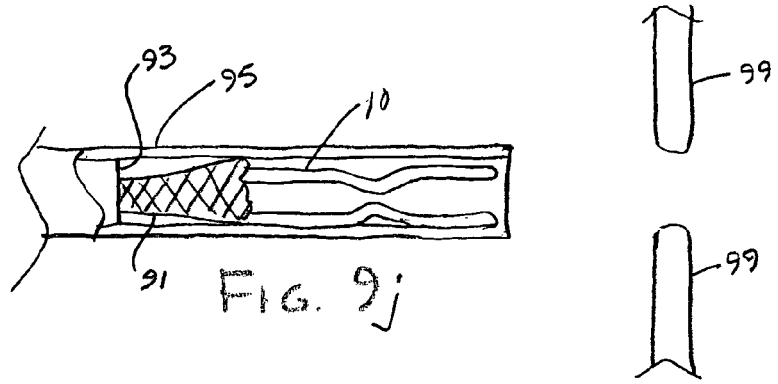

This is further described by the sequential side views of FIGS. 9d-9j. This sequence shows an occluder device 10 that has just been delivered and deployed at a site (e.g., a septal defect 99) in a fashion that is determined by the practitioner to be unacceptable, resulting in a desire to remove device 10. Device 10, as shown, is an embodiment including a purse string 98 extending back to the practitioner. To effect removal of device 10, the practitioner maintains slight tension on purse string 98 while moving catheter 95 back into close proximity to device 10 (FIG. 9d). Inner catheter 93 is moved distally with respect to outer catheter 95, thereby allowing snare 91 to extend and self expand (FIG. 9e). Applying further tension to purse string 98 collapses the adjacent side of device 10, allowing it to be withdrawn into snare 91 (FIGS. 9f-9g). Inner catheter 93 is then withdrawn back into outer catheter 95, pulling snare 91 and retrieved device 10 back into outer catheter 95 as well (FIGS. 9h-9j).

It is apparent that such a snare device 91 may have utility for the retrieval of various medical devices or implements or biological components.

Different examples were manufactured to create devices of various types. These were typically heat-treated at relatively low temperatures for relatively long times following forming of the filament to a desired shape. The heat treating process was designed to set (or anneal) the previously modified shape of the nitinol wire without causing significant damage to the polymer coating. In some cases, the temperature and time of the heat-treating process were also chosen to cause melting of a thermoplastic material to enable bonding together of adjacent, contacting filaments coated with the thermoplastic material. Several of the devices described by the examples were heat treated several times due to particular examples involving more than one filament-forming steps. The total heat exposure from all heat-treatment was intended to keep the $A_f$ of the nitinol alloy used below 37° C.

Example 1(a)

Nitinol wire was obtained (P/N SE-508, 0.127 mm diameter, Nitinol Devices and Components, Fremont Calif.). A composite ePTFE-FEP film was also obtained. One side of ePTFE film was discontinuously coated with FEP, wherein the FEP subsequently served as a melt adhesive. This coated fluoropolymer tape was made by a process which comprises the steps of:

a) contacting a porous PTFE substrate, usually in the form of a membrane or film, with a layer, usually a film of a thermoplastic fluoropolymer;

b) heating the composition obtained in step a) to a temperature above the melting point of the thermoplastic fluoropolymer;

c) stretching the heated composition of step b) while maintaining the temperature above the melting point of the thermoplastic fluoropolymer; and d) cooling the product of step c).

Either continuously coated (non-porous) or discontinuous (porous) coatings may be provided by this process. The discontinuous nature of the chosen FEP coating afforded a very thin composite film having a thickness of about 0.01 mm and a bulk density of about 0.3 g/cc. The composite film was slit to a width of about 19 mm and was then helically served onto a long length of rotating nitinol wire at a wrap angle of about 45 degrees from the longitudinal (length) axis of the wire. The nitinol wire was gripped at its ends with two heads rotating at the same speed. The amount of overlap was approximately 17 mm. About ten layers were wound onto the wire. The wrapping was performed such that the PTFE side was against the wire and the FEP adhesive side faced outward.

The film-covered wire was next wound on a pin jig as shown in FIG. 1a. The pin jig was created by press-fitting short, small diameter (3.0 mm long, 0.7 mm diameter) stainless steel pins into holes drilled in the surface of a 15.8 mm diameter stainless steel mandrel. The pins protruded about 1 mm from the surface of the mandrel. The pins were arranged in two rows of 13 equally-spaced pins each, with the pins of the two rows being aligned parallel to the longitudinal axis of the mandrel. The rows of pins were spaced 22.2 mm apart as measured parallel to the longitudinal axis of the mandrel. The covered wire was wound around the pins, with each successive revolution of winding around the mandrel that followed the first revolution involving laying covered wire on top of covered wire that had already been wound around the pins (generally as depicted in FIG. 1b). At no time was the wire woven or braided with itself or other wire strands. That is, the filament was never interlocked with other portions of itself during the winding process. The free end of the wire was never passed underneath wire previously wound around the pins during the winding process.

The winding was performed such that the wire was wound at a constant angle greater than zero degrees relative to the longitudinal axis of the jig. In the case of the present example, the winding pattern consisted of winding from a first pin located at a first end of the mandrel to a pin at the opposite end of the mandrel, with the pin at the opposite end of the mandrel located two pins circumferentially beyond the pin at the first end of the mandrel. The amount of circumferential offset chosen remained constant for the entire wrapping procedure. Generally, increased circumferential offset reduced the longitudinal stiffness of the device and increased the radial stiffness.

The fixture was then placed into a forced air oven set to 320° C. for a period of 30 minutes. This heat treatment melted the FEP coating on the film, thereby bonding the wire together at the crossover points, producing a wire frame. The heat-treating step also thermally set the shape of the wire. After this heat treatment step, the fixture with the wire frame still attached was quenched in water at room temperature or slightly less. The wire frame was removed from the mandrel and the ends were trimmed. The resulting device was able to be radially compressed and restrained by suitable means including, but not limited to, a restraining sheath or catheter, and thereby serve as a self-expanding stent.

Example 1(B)

Further processing of the stent of Example 1(a) was performed in order to convert it into a covered stent. An ePTFE tube having an inner diameter and wall thickness of about 13 mm and 0.1 mm, respectively, was slipped over a 15.8 mm stainless steel mandrel. The ePTFE tube was only intended to serve as a means of readily removing the covered stent from the mandrel subsequent to heat treatment. About two layers of the same ePTFE-FEP composite film as described above were applied to the outer surface of the ePTFE tube. The film was applied such that the FEP side was against the stent frame. The layers were applied in a "cigarette wrap" fashion with the primary strength direction of the film aligned with the longitudinal axis of the mandrel. Next, the stent was slipped over the tube- and film-covered mandrel, followed by adding two more layers of the composite film on top of the stent. Again, the film was applied such that the FEP side was against the stent frame. About two layers of an ePTFE film having a thickness of about 0.1 mm were wrapped on top of the composite film. The assembly was next placed in a forced air oven set to 320° C. for a period of 30 minutes. The heat-treated assembly was subsequently water quenched, followed by unwinding (i.e., removing) the outer ePTFE film and discarding it. The device was then removed from the mandrel and the inner ePTFE tube was removed and discarded. Loose ends of the film were trimmed. The resulting device was a covered stent (i.e., a stent-graft). It was able to be radially compressed and restrained by suitable means including, but not limited to, a restraining sheath or catheter, and thereby serve as a self-expanding covered stent.

Example 1(C)

The covered stent article of Example 1(b) was modified to create a variety of occluder devices. In one case, a fully-flared shape as depicted in FIGS. 4c and 4d was created using the shaping device described in FIG. 3a in order to fashion a device designed for interventional closure of cardiac septal defects (i.e., patent foramen ovale, atrial septal defect, ventricular septal defect).

A shaping tool was constructed of a stainless steel mandrel, two cylindrical aluminum shaping collars, and two cylindrical aluminum locking collars affixed to the mandrel with set screws.

The mandrel had a diameter of 3.0 mm and the shaping collars had inner and outer diameters of 3.2 mm and 15.9 mm, respectively. The locking collars had inner and outer diameters of 3.2 mm and 9 mm, respectively. The edges of the shaping collars were chamfered. The shaping collars were spaced 2.0 mm apart and prevented from moving apart from one another with the locking collars. The covered stent was placed over the shaping collars and positioned so that the center of the covered stent was aligned with the middle of the gap between the shaping collars as indicated in FIG. 3b. An ePTFE fiber was wrapped around the center of the device, thereby cinching the covered stent against the mandrel while also flaring the ends of the covered stent. The fiber was wrapped a few more times about the cinch point to secure the free end. The shaping collars were tightly pushed together and held by the locking collars, thereby securing the cinched waist during further processing as shown in FIGS. 4a and 4b. The assembly was placed in a forced air oven set to 320° C. for a period of 90 minutes and subsequently water quenched. The collars were spread apart, the cinching fiber was removed, and the collars and the now-completed occluder device were then removed from the mandrel. The device had a central orifice of about the diameter of the mandrel. FIGS. 4c and 4d illustrate the device.

A device made in accordance with the teachings of this example was cohesively disassembled by holding one end of the device between the fingers of one hand and gently applying a tensile force to the free end of the filament at the other end. Disassembly consisted of sequentially disrupting the bonds at the crossover points while simultaneously tearing the device covering material. (The precursor stent and covered constructs can obviously also be cohesively disassembled since this more complex design lends itself to such a procedure.)

Example 1(D)

Another covered stent made in accordance with the teachings above was also formed into an occluder device using the shaping device described in FIG. 3a. In this case the final device was in the shape of an hourglass, as depicted in FIG. 6. Such devices are suitable for, but not limited to, occluding or restricting flow in blood vessels.

An occluder device was made in the same manner as in Example 1(c) except that the shaping collars were spaced further apart (approximately 3 mm). The covered stent was placed over the shaping collars and centered on the gap. Both ends of the covered stent were then wrapped with about ten layers of an ePTFE film having a thickness of about 0.1 mm. This film is intended to hold the covered stent in place upon the shaping collars. An ePTFE fiber was looped around the center of the device, thereby cinching the covered stent against the mandrel. Since in this example, the ends of the device cannot flare (as in Example 1(c)), the collars are drawn closer together by this cinching step. The fiber was wrapped a few more times about the cinch point and tied. After the locking collars were repositioned against the shaping collars, the entire fixture was heat treated and quenched in accordance with Example 1(c).

Example 1(E)

Another covered stent made in accordance with the above teachings was formed into an occluder device. This device was pumpkin-shaped as shown in FIG. 7b and was made with the shaping device of FIG. 7a. This device also has utility for the occlusion of blood vessels.

An occluder device was made in the same manner as in Example 1(c) except that three shaping collars are employed. The middle-shaping collar (as shown by FIG. 7a) is rounded on both ends. The stent graft is placed upon the shaping collars and centered (longitudinally) over the center collar. On each side of the central collar, an ePTFE fiber was looped around the device, thereby cinching the covered stent against the mandrel. The fiber was wrapped a few more times about the cinch point and tied. After the locking collars were repositioned against the shaping collars the entire fixture was heat-treated and quenched in accordance with Example 1(c). The device was sprung open at one end to allow central shaping collar to be removed. The resilience of the device enabled the end of the device to return to its heat-treated shape. The finished device was removed from the rest of the tooling.

Example 2

A goblet-shaped occluder device was made. The shaping tool and the device are shown in FIGS. 5a and 5c, respectively. A covered frame was made in accordance with the teachings of Example 1(b) and then fashioned into an occluder.

An occluder device was made in the same manner as in Example 1(c) save for a few exceptions. In this example the large end of the covered stent was secured to the collar via several wrappings of an ePTFE film so that it did not flare as the center of the covered stent was cinched against the mandrel. Securing one end of the covered stent in this manner results in occluder devices that are asymmetric along their length. Furthermore, film was applied to the center of the device in order to cover the orifice.

Next, the center orifice was covered with ePTFE film. A high strength ePTFE film was used, as exemplified by films made according to U.S. Pat. No. 5,476,589 to Bacino, to which a discontinuous coating of FEP was applied as described previously. Four layers of the composite film were stacked at a 90 degree stacking angle atop the center orifice and secured in place using a heated soldering iron applied around the outer perimeter of the orifice. Excess film material was then trimmed from the final assembly and the edges tacked down thoroughly with the heated soldering iron, thereby completing the covering of the orifice. When punctured and dilated, the resultant orifice covering acted as an iris in somewhat of a scissors fashion rather than tearing and fraying.

In clinical applications, the covered center orifice could be retained intact in order to prevent any fluid flow across the device or it could be punctured subsequent to implantation. Such a device could have utility in the treatment of a neurovascular aneurysm. Aneurysms in the neurovasculature are typically sacular in shape, often called "berry aneurysms" since they are commonly found on the side of the host vessel. Treatment for this type of aneurysm is performed by filling the sac with multiple micro-coils. These coils are commonly made of platinum and some incorporate Dacron™ fibers in order to initiate a clotting response once implanted. Unfortunately, it commonly requires multiple coils to effect treatment. When applied to a so-called "large neck" aneurysm, these coils may migrate out into the host vessel. Treating the aneurysm with a miniature occlusion device of this example would be much preferred. The puncturable and re-crossable orifice would allow the subsequent use of coils if so desired.

Larger sizes of this device may be useful in left atrial appendage applications.

Example 3

A pin jig was created by press-fitting short, small diameter (3.0 mm long, 0.7 mm diameter) stainless steel pins into mating holes drilled into the surface of a 25.4 mm diameter stainless steel mandrel. The pins were arranged in two rows of 19 pins each such that the pins of the two rows were aligned parallel to the axis of the jig. Each row of 19 pins was spaced 20 mm apart (as measured parallel to the longitudinal axis of the mandrel).

A length of ePTFE thread was wound upon the pin jig (between the pins). This thread is intended to be used as a release agent, to assist in the release of the device from the mandrel once processing is complete. A length of stainless steel wire (0.51 mm diameter) was obtained and wound upon the pin jig. As described previously, the wire was wound around the pins, always laying covered wire on top of covered wire that had already been wound around the pins.

The entire device was the coated with a layer of silicone. The silicone (NuSil, Med-1137, Type A, Carpenteria Calif.) was applied by spatula and smoothed by rotating the fixture while holding the spatula blade against the device.

The device was allowed to cure at room temperature for approximately 24 hours, after which it was stripped from the mandrel by pulling the pins from the mandrel and unwrapping the ePTFE thread from beneath the device.

This device, once compacted, will stay at a reduced dimension without constraint until it is intentionally distended, such as by inflation of a balloon. In this tubular configuration it can serve well as a stent-graft.

Example 4

Nitinol wire was obtained (P/N SE-508, 0.2 mm diameter, Nitinol Devices and Components, Fremont Calif.). A composite ePTFE-FEP film was wrapped around the wire as described previously in Example 1(a).

Figure 10A:
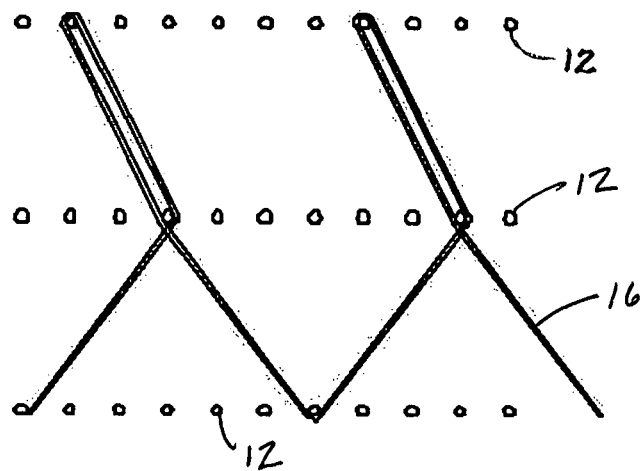
FIG. 10a is a longitudinal cross-section of an alternative pin jig layout having three rows of pins.

The film-covered wire was next wound on a pin jig. The pin jig was created by press-fitting short, small diameter (3.0 mm long, 0.7 mm diameter) stainless steel pins into a 25.4 mm diameter stainless steel mandrel as described in Example 3. The pins were arranged in three circumferential rows of 7 each such that the pins of the three rows were aligned parallel to the axis of the jig as indicated in FIG. 10a. Each row of 7 pins was spaced 20 mm apart (as measured parallel to the longitudinal axis of the mandrel). The covered wire was wound around the pins as described previously, wherein after full turn around the surface of the mandrel had been completed (resulting in a completed first winding layer), continued winding resulted in laying covered wire on top of covered wire that had already been wound around the pins. As in the previous examples, once the number of full passes around the circumference equaled the number of pins positioned around the circumference, the lay-up of the device was complete.

The fixture was then placed in a forced air oven set to 320° C. for a period of 30 minutes. This heat treatment melted the FEP coating on the film, thereby bonding the wire together at the crossover points, producing a wire frame. The heat-treating step also thermally set the shape of the wire. After this heat treatment step, the fixture with the wire frame still attached was quenched in water. The wire frame was removed from the mandrel and the ends were trimmed.

Figure 10B:
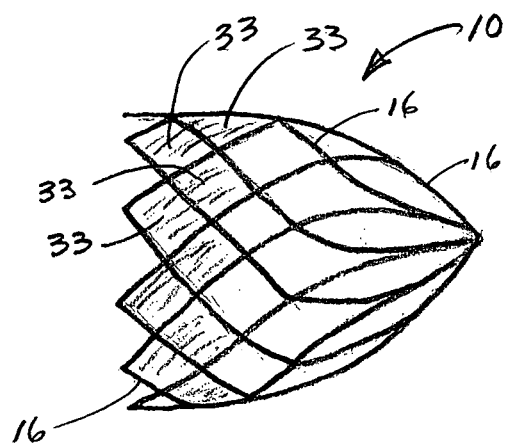
FIG. 10b is a side view of a vena cava filter device made on a pin jig having three rows of pins.

Further processing was performed in order to provide a vena cava filter. An ePTFE tube having an inner diameter and wall thickness of about 24 mm and 0.1 mm, respectively, was slipped over a 25.4 mm stainless steel mandrel. The properties of the ePTFE tube are not critical inasmuch as it serves primarily as a means of readily removing the covered stent from the mandrel subsequent to heat treatment. About two layers of the same ePTFE-FEP composite film as described above were applied to the outer surface of the ePTFE tube. The film was applied such that the FEP side was against the stent frame. The layers were applied in a "cigarette wrap" fashion with the primary strength direction of the film aligned with the longitudinal axis of the mandrel. Next, the stent was partially slipped over the tube- and film-covered mandrel, followed by adding two more layers of the composite film on top of the stent. Again, the film was applied such that the FEP side was against the stent frame. About two layers of an ePTFE film having a thickness of about 0.1 mm were wrapped on top of the composite film. The "free" apices of the device at its distal end were tied together with a piece of ePTFE thread in a "purse-string" style knot, resulting in the conical configuration shown in the side view of FIG. 10*b*.

The assembly was next placed in a forced air oven set to 320° C. for a period of 30 minutes. The heat-treated assembly was subsequently water quenched, followed by unwinding (i.e., removing) the outer ePTFE film and discarding it. The device was then removed from the mandrel and the inner ePTFE tube was removed and discarded. Loose ends of the film were trimmed. The resulting device has utility as a partially covered inferior vena cava filter.

Examples 5(a), 5(B) and 5(C)

Example 5(a) was made using the same process as described in Example 1(a); Example 5(b) was made using the same process as described in Example 1(b). For Example 5(c), the covered stent article of Example 5(b) was modified to create a variety of occluder devices. In one case, a fully-flared shape as depicted in FIG. 4*c* was created using the shaping fixture incorporating an iris to effect the cinching of the covered stent. The resulting device of the present invention has utility for medical procedures such as in treating patent foramens ovale.

A shaping fixture was constructed of a stainless steel mandrel, two cylindrical stainless steel shaping mandrels, and an Iris positioned at the center. The shaping mandrels had outer diameters of 15.9 mm and were hollow to allow rapid heating and cooling. The edges of the shaping mandrels were chamfered. The shaping mandrels were spaced 2.0 mm apart and prevented from moving apart from one another with setscrews. The covered stent was placed over the shaping collars and positioned so that the center of the covered stent was aligned with the middle of the gap between the shaping collars. The iris (P/N 53911, Edmund Scientific, Barrington N.J.) was activated, thereby cinching the covered stent into the gap between the shaping mandrels while also flaring the ends of the covered stent. The shaping mandrels were tightly pushed together and again locked in place with setscrews, thereby securing the cinched waist during further processing. The assembly was placed in a forced air oven set to 320° C. for a period of 90 minutes and subsequently water quenched. The shaping mandrels were spread apart, the iris opened, and the now-completed occluder device was then removed from the fixture. The device in this case had a minimal orifice.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. An implantable device comprising a self-expanding filament-wound tubular structure having a circumference, opposing proximal and distal ends, and a crossing pattern of at least one filament having a length,
    wherein said filament includes a multiplicity of filament portions defined as portions of the length of the filament separated by consecutive apices along the length of the filament, said apices comprising bent portions of said filaments located only at the opposing proximal and distal ends of said tubular structure,
    wherein the crossing pattern is non-interlocking and includes multiple crossover points along a length of a filament portion,
    wherein the filament is wound only on top of previously wound filament and does not pass underneath previously wound filament such that the filament is not woven or braided, and
    wherein no filament portion extends around the entire circumference of the tubular structure.

2. The implantable device of claim 1 wherein the non-interlocking crossing pattern allows the expandable structure to be removed after deployment by pulling on one end of the filament.

3. The implantable device of claim 1 wherein the crossing pattern includes bonded crossover points.

4. The implantable device of claim 3 wherein the filament comprises nitinol wire.

5. The implantable device of claim 4 wherein the nitinol wire has an outer surface of which at least a portion is provided with a covering of polytetrafluoroethylene.

6. The implantable device of claim 1 wherein the filament comprises nitinol wire.

7. The implantable device of claim 6 wherein the nitinol wire has an outer surface of which at least a portion is provided with a covering of polytetrafluoroethylene.

8. The implantable device of claim 1 configured for use as a stent.

9. The implantable device of claim 8 wherein the crossing pattern includes bonded crossover points.

10. The implantable device of claim 8 wherein the filament comprises nitinol wire.

11. The implantable device of claim 1 configured for use as a stent-graft.

12. The implantable device of claim 11 wherein the crossing pattern includes bonded crossover points.

13. The implantable device of claim 11 wherein the filament comprises nitinol wire.

14. The implantable device of claim 1 configured for use as an occluder.

15. The implantable device of claim 14 wherein the crossing pattern includes bonded crossover points.

16. The implantable device of claim 14 wherein the filament comprises nitinol wire.

17. The implantable device of claim 1 configured for use as a vena cava filter.

18. The implantable device of claim 17 wherein the crossing pattern includes bonded crossover points.

19. The implantable device of claim 17 wherein the filament comprises nitinol wire.

20. The implantable device of claim 1 wherein the tubular structure defines a shape having a pair of opposing planar forms each having a generally circular shape oriented to be substantially transverse to a longitudinal axis of the tubular structure, said opposing planar forms having a diameter and interconnected by a waist having a diameter less than the diameters of the opposing planar forms.

21. An implantable device according to claim 20 wherein the waist includes an orifice extending through a center portion thereof.

22. An implantable device according to claim 21 wherein the device is removable intact by being withdrawn into a catheter.

23. An implantable device according to claim 21 wherein the device is formed of a single filament.

24. An implantable device according to claim 23 wherein the device is removable intact by being withdrawn into a catheter.

25. An implantable device according to claim 23 wherein the device is formed of a single filament.

26. An implantable device according to claim 25 wherein the device is removable from a body in which it has been implanted by being withdrawn into a catheter.

27. An implantable device according to claim 26 wherein the device is removable by being disassembled and withdrawn into the catheter.

28. An implantable device according to claim 20 wherein the device is removable from a body in which it has been implanted by being withdrawn into a catheter.

29. An implantable device according to claim 20 wherein the device is removable intact by being withdrawn into a catheter.

30. An implantable device according to claim 20 wherein the device further comprises a graft covering material over an outer surface of the device.

31. An implantable device according to claim 30 wherein the graft covering material comprises ePTFE.

32. An implantable device according to claim 20 wherein the device further comprises a graft covering material over an inner surface of the device.

33. An implantable device according to claim 32 wherein the graft covering material comprises ePTFE.

34. An implantable device according to claim 20 wherein the device further comprises a graft covering material over both an outer surface and inner surface of the device.

35. An implantable device according to claim 34 wherein the graft covering material comprises ePTFE.

* * * * *